(12) United States Patent
Seayad et al.

(10) Patent No.: US 6,479,693 B2
(45) Date of Patent: Nov. 12, 2002

(54) PROCESS FOR THE PREPARATION OF A SATURATED CARBOXYLIC ACID

(75) Inventors: Jayasree Seayad, Pune (IN); Abdul Majeed Seayad, Pune (IN); Bibhas Ranjan Sarkar, Pune (IN); Raghunath Vitthal Chaudhari, Pune (IN)

(73) Assignee: Council of Scientific and Industial Research, New Delhi (IN)

( * ) Notice: Subject to any disclaimer, the term of this patent is extended or adjusted under 35 U.S.C. 154(b) by 0 days.

(21) Appl. No.: 09/813,086

(22) Filed: Mar. 20, 2001

(65) Prior Publication Data

US 2002/0137964 A1 Sep. 26, 2002

(51) Int. Cl.$^7$ ................................ C07C 69/76
(52) U.S. Cl. .................... 560/100; 560/105; 560/106; 560/109
(58) Field of Search .............. 560/8, 100, 109, 560/114, 129, 130, 233, 105, 106; 502/155, 162

(56) References Cited

U.S. PATENT DOCUMENTS 5,315,026 A * 5/1994 Wu .............................. 560/105
6,025,295 A * 2/2000 Tanielyan et al. ........... 502/154
6,069,253 A * 5/2000 Chaudhari et al. ............. 546/2

OTHER PUBLICATIONS

M. Dolors Miquel–Serrano et al, "Recoverable chiral palladium–sulfonated diphosphine catalysts for the asymmetric hydrocarboxylation of vinyl arenes" Tet. Asym., vol. 10 (1999), pp. 4463–4467.*

* cited by examiner

Primary Examiner—Paul J. Killos
(74) Attorney, Agent, or Firm—Ladas & Parry

(57) ABSTRACT

The present invention relates to a process for the preparation of a carboxylic acid ester of the general formula II,

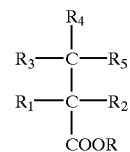

Formula II wherein R is alkyl or aryl, $R_1$ is aryl, substituted aryl, naphthyl or substituted naphthyl or alkyl, $R_2$, $R_3$, $R_4$ and $R_5$ are independently hydrogen or alkyl by reacting an olefin of the general formula I

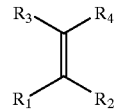

Formula I wherein, $R_1$ is aryl, substituted aryl, naphthyl or substituted naphthyl or alkyl, $R_2$, $R_3$, and $R_4$ are independently hydrogen or alkyl, in the presence of an alcohol and an organic solvent and a supported aqueous phase palladium complex catalyst, in presence or absence of a protonic acid and an alkali metal halide, under carbon monoxide atmosphere, cooling the reaction mixture to ambient temperature, depressurising the reactor, flushing the reaction vessel with inert gas, separating the catalyst by filtration and removing the solvent and isolating the compound of formula II.

25 Claims, No Drawings

PROCESS FOR THE PREPARATION OF A SATURATED CARBOXYLIC ACID

FIELD OF THE INVENTION

The present invention relates to a process for the preparation of a saturated carboxylic acid ester. More particularly, the present invention relates to a process for the conversion of olefins of the general formula I

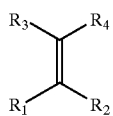

Formula I wherein, $R_1$ is aryl, substituted aryl, naphthyl or substituted naphthyl or alkyl, $R_2$, $R_3$ and $R_4$ are independently hydrogen or alkyl, to an ester of the corresponding saturated carboxylic acid of the general formula II

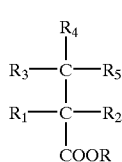

Formula II wherein, R is alkyl or aryl, $R_1$ is aryl, substituted aryl, naphthyl or substituted naphthyl or alkyl, $R_2$, $R_3$, $R_4$ and $R_5$ are independently hydrogen or alkyl, using a supported aqueous phase palladium complex catalyst.

BACKGROUND OF THE INVENTION

Aryl and aliphatic saturated carboxylic acid esters have a variety of applications in industries as, anti-inflammatory drugs, fine chemicals etc. The prior art describe catalyst systems for employment in processes for the preparation of esters of carboxylic acids by the alkoxy carbonylation of corresponding olefins. The best known of such catalysts are homogeneous palladium catalysts. In general, the catalyst systems used for the alkoxycarbonylation of olefins contain a palladium source, a phosphine ligand and a hydrogen halide promoter. Alkoxycarbonylation of olefins using a catalyst system comprising $PdCl_2$ or $PdCl_2(PPh_3)_2$, excess triphenylphosphine and HCl has been found to occur only at drastic conditions such as 300–700 atm of CO pressure (Bittler et. al., Angew. Chem. Internat. Ed., 7, 1968, 329). Oi et. al. (J. Mol. Cat. A: Chem., 115, 1997, 289) have reported hydroesterification of styrene using cationic palladium complexes and which proceeds under mild conditions (20 atm, 80° C.) to give 91–94% product yield in four hours (TOF=11 $h^{-1}$) with n: iso ratio of 60:40. Recently Seayad et al, (Ind. Eng. Chem. Res., 37, 1998, 2180, J. Mol. Catal. A: Chem., 151, 2000, 47–59) have shown enhanced reaction rates in the hydroesterification of styrene (TOF=411 $h^{-1}$) using a catalyst system comprising of $Pd(OAc)_2$, $PPh_3$ and p-toluene sulphonic acid with an n:iso ratio of 35:64. A major disadvantage of these homogeneous catalytic processes was the difficulty in separation of the catalyst from the product and its recycle. An important method for heterogenizing such homogeneous catalysts is the application of two-phase systems comprising an aqueous phase containing water-soluble organometallic catalysts and a water immiscible phase (U.S. 31812; Kuntz E. G. CHEMTECH 17, 1987, 570; EP 0107006; B. Cornils, W. A. Herrmann (Eds.), Aqueous-Phase Organometallic Catalysis, Wiley-VCH, 1998, Weinheim). In this case, separation of the organometallic catalyst from the organic reactants and products is greatly simplified due to the insolubility of the catalyst in water immiscible phase.

Supported Aqueous Phase Catalysis (SAPC) (U.S. Pat. Nos. 5,736,980, 5,935,892) is another method to heterogenize homogeneous catalysts. Here, the catalytic material consists of a thin film of water containing a metal complex catalyst spread over a high-surface-area inorganic support, such as silica. The molecular catalyst is immobilized via the solvent i.e. water, reactants and products being in the organic phase. The main advantages of the SAP catalysts are easy catalyst recovery and good activity because of the high interfacial area, a property particularly sensitive with sparingly water-soluble reactants (J. P. Arhancet, M. E. Davis, J. S. Merola, Be. Hanson, Nature, 339, 1989, 454; K. T. Wan, M. E. Davis, Nature, 370, 1994, 449; K. T. Wan, M. E. Davis, J. Catal., 148, 1994, 1).

OBJECTS OF THE INVENTION

The object of the present invention therefore is to provide an improved process for the preparation of carboxylic acid esters by the alkoxycarbonylation of corresponding olefins using supported aqueous phase palladium complex catalysts.

It is another object of the invention to provide a process for the preparation of a saturated carboxylic acid ester that overcomes the drawbacks of the prior art enumerated above.

It is another object of the invention to provide a process for the preparation of a carboxylic acid ester that results in good yield and selectivity to carboxylic acid esters.

It is a further object of the invention to provide a process for the preparation of a carboxylic acid ester that provides simple and efficient catalyst separation and recycle.

It is observed in the invention that the use of supported aqueous phase palladium complex catalysts provide an improved catalyst for the carbonylation of olefins to corresponding saturated carboxylic acid esters. The use of such a catalyst gives good yields of carboxylic acid esters under mild reaction conditions with easy separation and reuse of the catalyst.

SUMMARY OF THE INVENTION

Accordingly, the present invention provides a process for the preparation of a carboxylic acid ester of the general formula II,

Formula II wherein R is alkyl or aryl, $R_1$ is aryl, substituted aryl, naphthyl or substituted naphthyl or alkyl, $R_2$, $R_3$, $R_4$ and $R_5$ are independently hydrogen or alkyl, said process comprising reacting an olefin of the general formula I

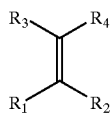

Formula I wherein, $R_1$ is aryl, substituted aryl, naphthyl or substituted naphthyl or alkyl, $R_2$, $R_3$, and $R_4$ are independently hydrogen or alkyl, in the presence of an alcohol and an organic solvent and a supported aqueous phase palladium complex catalyst, in presence or absence of a protonic acid and an alkali metal halide, under carbon monoxide atmosphere, at a temperature ranging between 30 to 130° C., for a period ranging between 1–72 hours, at pressures ranging between 50 to 1500 psig, cooling the reaction mixture to ambient temperature, depressurising the reactor, flushing the reaction vessel with inert gas, separating the catalyst by filtration and removing the solvent and isolating the compound of formula II.

In one embodiment of the present invention, the catalyst used comprises a watersoluble palladium complex with or without free sufonated phosphine ligand.

In another embodiment of the invention, the water soluble palladium complex used are selected from the group consisting of any of Pd(II) and Pd(0) compounds of the type $Pd^{II}(OAc)_2P_2$, $Pd^{II}P_2Cl_2$, $Pd^{II}P_3Cl]^+Cl^-$, $Pd^0P_2$, $Pd^0P_3$ and mixtures thereof; wherein P is a sulfonated phosphine ligand; or a complex of the general formula III

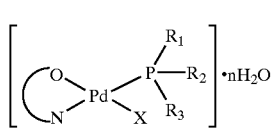

Formula III wherein $R_1$, $R_2$ and $R_3$ are substituents on the phosphine ligand and selected from the group consisting of alkyl, aryl, arylalkyl, cycloaliphatic, at least one of which carries a sulfonic acid, and salts thereof, X is aryl or alkyl sulfonato or aryl or alkyl carboxylate or formato or halides such as $Cl^-$, $Br^-$, $I^-$,

is an anionic chelating ligand containing a N donor and $O^-$ group.

In a further embodiment of the invention, said anionic chelating ligand is selected from the group consisting of 8-hydroxyquinoline, 2-hydroxypyridine, (2-hydroxyethyl)pyridine, pyridil-2-, pyrezyl-2, piperidyl-2-, piperzyl-2-, quinolyl-2-, isoquinolyl-1- and isoquinolyl-2-carboxylates, particularly pyridyl-2-carboxylate, piperidyl-2-carboxylate and 8-hydroxyquinoline.

In another embodiment of the present invention, the support used for the preparation of the supported aqueous phase palladium complex catalyst is selected from porous or nonporous silica.

In yet another embodiment the sulfonated phosphorous ligand used for the preparation of the supported aqueous phase catalyst comprises a sulfonated mono phosphines.

In a further embodiment of the invention, the sulfonated mono phosphine is selected from the group consisting of tris(sodium 3-sulfonatophenyl)phosphine (TPPTS), phenylbis(sodium-3-sulfonatophenyl)phosphine (TPPDS), diphenyl (sodium-3-sulfonatophenyl)phosphine (TPPMS), methylbis(3-sulfonatophenyl)phosphine, cyclohexylbis (sodium-3-sulfonatophenyl)phosphine, isopropyl bis (sodium-3-sulfonatophenyl)phosphine, dimethyl(sodium-3-sulfonatophenyl)phosphine and dicyclohexyl(3-sulfonatophenyl)phosphine.

In another embodiment the amount sulfonated phosphine ligand used per gram mole of palladium for the preparation of the supported aqueous phase palladium catalyst may be 1–20 moles, preferably 2–6 moles.

In another embodiment of the present invention, the protonic acid used for the alkoxycarbonylation reaction is selected from a hydro halic acids or a protonic acids.

In a further embodiment of the invention, the hydrohalic acid is selected from the group consisting of hydrochloric acid, hydrobromic acid and hydro iodic acid.

In a further embodiment of the invention, the protonic acid is selected from the group consisting of para toluene sulphonic acid, methane sulphonic acid, triflouromethane sulphonic acid, formic acid, oxalic acid, acetic acid and trifluoro acetic acid.

In yet another embodiment the halide source used for the alkoxycarbonylation reaction a halide salt or a hydrohalic acid.

In a further embodiment of the invention, the halide salt is selected from the group consisting of lithium chloride, sodium chloride, potassium chloride, lithium iodide, lithium bromide, sodium bromide, sodium iodide, potassium bromide, potassium iodide, tetrabutylammonium chloride, tetrabutylammonium bromide and tetrabutylammonium iodide.

In another embodiment of the present invention, the hydrohalic acid is selected from the group consisting of hydrochloric acid, hydrobromic acid and hydroiodic acid.

In another embodiment the alcohol used for the alkoxycarbonylation reaction is selected from the group consisting of methanol, ethanol, n- or iso propanol, n-, iso- or tert-butanol, higher alcohols and phenols.

In yet another embodiment the organic solvent for the alkoxycarbonylation reaction is selected from the group consisting of cyclohexane, benzene, toluene, xylenes, petroleum ether, hexane, heptane and decane.

In another embodiment the concentration of catalyst is one mole of catalyst for every 50 to 50000 moles of substrate.

In a further embodiment of the invention, the concentration of the catalyst is 1 mole of catalyst for every 100 to 10000 moles of substrate, more preferably one mole of catalyst for every 150 to 5000 moles of substrate.

In still another embodiment the amount of halide source if used per gram mole of catalyst is in the range of 1 to 50 moles, preferably 5 to 10 moles.

In another embodiment the amount of acid source if used per gram mole of catalyst is in the range of 1 to 50 moles, preferably 5 to 10 moles.

In a feature of the invention, the reaction is carried out in a stirred reactor with the improved catalyst employed with a suitable solvent in presence of carbon monoxide.

DETAILED DESCRIPTION OF THE INVENTION

The improved process of the present invention is described herein below with examples, which are illustrative only and should not be construed to limit the scope of the present invention in any manner.

EXAMPLE 1
Preparation of SAP Catalyst A 0.0937 mmol of the palladium complex of formula IV in which $R'_1$, $R'_2$, $R'_3$=phenyl, X=p-toluenesulfonato (TsO$^-$),=pyridyl-2-carboxylate (prepared as the procedure given in the U.S. Pat. No. 6,069,253) was dissolved in methyl ethyl ketone (MEK) (7 ml) and shaken vigorously with 3 equivalents of TPPTS {tris(m-sulfophenyl)phosphine trisodium salt} in degassed water (3 ml). The yellow colour of the MEK layer disappeared and the aqueous layer became yellow in colour indicating the formation of the palladium complex of formula IIIa, in water which was added to 1 g of the degassed dehydroxylated (kept at 523 K under vacuum for 5–6 hours) silica (BET Surface area=210 m$^2$/g) in a Schlenk flask and the wet solid was stirred for 2 h under argon. Water was then evaporated under high vacuum at constant stirring. A dry yellow powder was obtained which was stored under argon. The water content of the catalyst thus prepared was found to 10–12% (w/w) (as determined by TGA).

EXAMPLE 2
Preparation of SAP Catalyst B

Pd(OAc)$_2$ (0.094 mmol) and TPPTS (0.376 mmol) in 3 ml of degassed water were kept for stirring for 1–1.5 h to form Pd(TPPTS)$_3$ under argon. This solution was then added to 1 g of degassed dehydroxylated (kept at 523 K under vacuum for 5–6 hours)silica (BET Surface area=210 m$^2$/g) in a Schlenk flask and the wet solid was stirred for 2 h under argon. Water was then evaporated under high vacuum at constant stirring. A dry yellow powder was obtained which was stored under argon. The water content of the catalyst thus prepared was found to 10–12% (w/w) (as determined by TGA).

EXAMPLE 3
Alkoxycarbonylation of Styrene

A 50 ml stirred autoclave was charged with the following reactants

Styrene: 14.4 mmol

SAP Catalyst A: 150 mg

Methanol: 1 ml

The contents of the autoclave were flushed with nitrogen and then many times with carbon monoxide. Thereafter, the contents were heated to 75° C. After the temperature is attained, the autoclave was pressurised to 500 psig with carbonmonoxide, stirring started. For preparation of final methyl phenyl propionate product, the pressure in the autoclave was maintained constant and the progress of the reaction was monitored by observing the pressure drop and by liquid sampling. The reaction was continued for 12 hours. The reactor was then cooled and the liquid phase analysed by gas chromatography. The GC analysis showed TOF of 2.6 h$^{-1}$ and 3.1% conversion of styrene with the formation of a mixture of methyl 2-phenylproprionate and methyl 3-phenylproprionate with selectivity of 54.26% and 45.73% respectively. The alkoxycarbonylation products were then isolated by separating the catalyst by filteration and removing the solvents and remaining styrene by distillation.

EXAMPLE 4
Recycle 1

A 50 ml stirred autoclave was charged with the following reactants

Styrene: 14.4 mmol

SAP Catalyst A separated from Example 1: 120 mg

Methanol: 1 ml

Cyclohexane: 22 ml

The contents of the autoclave were flushed with nitrogen and then many times with carbon monoxide. Thereafter, the contents were heated to 75° C. After the temperature is attained, the autoclave was pressurised to 500 psig with carbonmonoxide, stirring started. For preparation of final methyl phenyl propionate product, the pressure in the autoclave was maintained constant and the progress of the reaction was monitored by observing the pressure drop and by liquid sampling. The reaction was continued for 12 hours. The reactor was then cooled and the liquid phase analysed by gas chromatography. The GC analysis showed TOF of 2.1 h$^{-1}$ and 3% conversion of styrene with the formation of a mixture of methyl 2-phenylproprionate and methyl 3-phenylproprionate with selectivity of 54% and 46% respectively. The alkoxycarbonylation products were then isolated by separating the catalyst by filtration and removing the solvents and remaining styrene by distillation.

EXAMPLE 5
Recycle 2

A 50 ml stirred autoclave was charged with the following reactants

Styrene: 14.4 mmol

SAP Catalyst A separated from the Example 4: 100 mg

Methanol: 1 ml

Cyclohexane: 22 ml

The contents of the autoclave were flushed with nitrogen and then many times with carbon monoxide. Thereafter, the contents were heated to 75° C. After the temperature is attained, the autoclave was pressurised to 500 psig with carbonmonoxide, stirring started. For preparation of final methyl phenyl propionate product, the pressure in the autoclave was maintained constant and the progress of the reaction was monitored by observing the pressure drop and by liquid sampling. The reaction was continued for 12 hours. The reactor was then cooled and the liquid phase analysed by gas chromatography. The GC analysis showed TOF of 1.8 h$^{-1}$ and 2.3% conversion of styrene with the formation of a mixture of methyl 2-phenylproprionate and methyl 3-phenylproprionate with selectivity of 54.3% and 45.7% respectively. The alkoxycarbonylation products were then isolated by separating the catalyst by filtration and removing the solvents and remaining styrene by distillation.

EXAMPLE 6
Recycle 3

A 50 ml stirred autoclave was charged with the following reactants

Styrene: 14.4 mmol

SAP Catalyst A separated from the Example 5: 70 mg

Methanol: 1 ml

Cyclohexane: 22 ml

The contents of the autoclave were flushed with nitrogen and then many times with carbon monoxide. Thereafter, the contents were heated to 75° C. After the temperature is attained, the autoclave was pressurized to 500 psig with carbonmonoxide, stirring started. For preparation of final methyl phenyl propionate product, the pressure in the autoclave was maintained constant and the progress of the reaction was monitored by observing the pressure drop and by liquid sampling. The reaction was continued for 12 hours. The reactor was then cooled and the liquid phase analysed by gas chromatography. The GC analysis showed TOF of 1.2 h$^{-1}$ and 1.5% conversion of styrene with the formation of a mixture of methyl 2-phenylproprionate and methyl 3-phenylproprionate with selectivity of 54% and 46 respectively. The alkoxycarbonylation products were then isolated by separating the catalyst by filtration and removing the solvents and remaining styrene by distillation.

EXAMPLE 7
Alkoxycarbonylation of Styrene

A 50 ml stirred autoclave was charged with the following reactants

Styrene: 14.4 mmol
SAP Catalyst A: 150 mg
Methanol: 1 ml
Toluene: 22 ml

The contents of the autoclave were flushed with nitrogen and then many times with carbon monoxide. Thereafter, the contents were heated to 75° C. After the temperature is attained, the autoclave was pressurized to 500 psig with carbonmonoxide, stirring started. For preparation of final methyl phenyl propionate product, the pressure in the autoclave was maintained constant and the progress of the reaction was monitored by observing the pressure drop and by liquid sampling. The reaction was continued for 12 hours. The reactor was then cooled and the liquid phase analysed by gas chromatography. The GC analysis showed TOF of 1.5 $h^{-1}$ and 1.85% conversion of styrene with the formation of a mixture of methyl 2-phenylproprionate and methyl 3-phenylproprionate with selectivity of 60.34% and 39.65 respectively. The alkoxycarbonylation products were then isolated by separating the catalyst by filtration and removing the solvents and remaining styrene by distillation.

EXAMPLE 8
Alkoxycarbonylation of Styrene

A 50 ml stirred autoclave was charged with the following reactants

Styrene: 14.4 mmol
SAP Catalyst A: 150 mg
TsOH: 0.10526 mmol
Methanol: 1 ml
Cyclohexane: 22 ml The contents of the autoclave were flushed with nitrogen and then many times with carbon monoxide. Thereafter, the contents were heated to 75° C. After the temperature is attained, the autoclave was pressurized to 500 psig with carbonmonoxide, stirring started. For preparation of final methyl phenyl propionate product, the pressure in the autoclave was maintained constant and the progress of the reaction was monitored by observing the pressure drop and by liquid sampling. The reaction was continued for 12 hours. The reactor was then cooled and the liquid phase analysed by gas chromatography. The GC analysis showed TOF of 18.9 $h^{-1}$ and 23% conversion of styrene with the formation of a mixture of methyl 2-phenylproprionate and methyl 3-phenylproprionate with selectivity of 74.16% and 25.83 respectively. The alkoxycarbonylation products were then isolated by separating the catalyst by filtration and removing the solvents and remaining styrene by distillation.

EXAMPLE 9
Alkoxycarbonylation of 4-isobutylstyrene

A 50 ml stirred autoclave was charged with the following reactants 4-isobutylstyrene: 14.4 mmol
SAP Catalyst A: 150 mg
TsOH: 0.10526 mmol
Methanol: 1 ml
Cyclohexane: 22 ml The contents of the autoclave were flushed with nitrogen and then many times with carbon monoxide. Thereafter, the contents were heated to 75° C. After the temperature is attained, the autoclave was pressurized to 500 psig with carbonmonoxide, stirring started. For preparation of final methyl phenyl propionate product, the pressure in the autoclave was maintained constant and the progress of the reaction was monitored by observing the pressure drop and by liquid sampling. The reaction was continued for 12 hours. The reactor was then cooled and the liquid phase analysed by gas chromatography. The GC analysis showed TOF of 15 $h^{-1}$ and 20% conversion of 4-isobutylstyrene with the formation of a mixture of methyl 2-phenylproprionate and methyl 3-phenylproprionate with selectivity of 75% and 25 respectively. The alkoxycarbonylation products were then isolated by separating the catalyst by filtration and removing the solvents and remaining styrene by distillation.

EXAMPLE 10
Alkoxycarbonylation of 4-methylstyrene

A 50 ml stirred autoclave was charged with the following reactants 4-methylstyrene: 14.4 mmol
SAP Catalyst A: 150 mg
TsOH: 0.10526 mmol
Methanol: 1 ml
Cyclohexane: 22 ml The contents of the autoclave were flushed with nitrogen and then many times with carbon monoxide. Thereafter, the contents were heated to 75° C. After the temperature is attained, the autoclave was pressurized to 500 psig with carbonmonoxide, stirring started. For preparation of final methyl phenyl propionate product, the pressure in the autoclave was maintained constant and the progress of the reaction was monitored by observing the pressure drop and by liquid sampling. The reaction was continued for 12 hours. The reactor was then cooled and the liquid phase analysed by gas chromatography. The GC analysis showed TOF of 18 $h^{-1}$ and 22% conversion of 4-methylstyrene with the formation of a mixture of methyl 2-phenylproprionate and methyl 3-phenylproprionate with selectivity of 74% and 26% respectively. The alkoxycarbonylation products were then isolated by separating the catalyst by filtration and removing the solvents and remaining styrene by distillation.

EXAMPLE 11
Alkoxycarbonylation of 4-chlorostyrene

A 50 ml stirred autoclave was charged with the following reactants 4-chlorostyrene: 14.4 mmol
SAP Catalyst A: 150 mg
TsOH: 0.10526 mmol
Methanol: 1 ml
Cyclohexane: 22 ml The contents of the autoclave were flushed with nitrogen and then many times with carbon monoxide. Thereafter, the contents were heated to 75° C. After the temperature is attained, the autoclave was pressurized to 500 psig with carbonmonoxide, stirring started. For preparation of final methyl phenyl propionate product, the pressure in the autoclave was maintained constant and the progress of the reaction was monitored by observing the pressure drop and by liquid sampling. The reaction was continued for 12 hours. The reactor was then cooled and the liquid phase analysed by gas chromatography. The GC analysis showed TOF of 15 h$^{-1}$ and 20% conversion of 4-chlorostyrene with the formation of a mixture of methyl 2-phenylproprionate and methyl 3-phenylproprionate with selectivity of 77% and 23% respectively. The alkoxycarbonylation products were then isolated by separating the catalyst by filtration and removing the solvents and remaining styrene by distillation.

EXAMPLE 12

Alkoxycarbonylation of Styrene

A 50 ml stirred autoclave was charged with the following reactants

Styrene: 14.4 mmol

SAP Catalyst A: 150 mg

TsOH: 0.10526 mmol

Methanol:1 ml

Cyclohexane: 22 ml

The contents of the autoclave were flushed with nitrogen and then many times with carbon monoxide. Thereafter, the contents were heated to 75° C. After the temperature is attained, the autoclave was pressurised to 200 psig with carbonmonoxide, stirring started. For preparation of final methyl phenyl propionate product, the pressure in the autoclave was maintained constant and the progress of the reaction was monitored by observing the pressure drop and by liquid sampling. The reaction was continued for 12 hours. The reactor was then cooled and the liquid phase analysed by gas chromatography. The GC analysis showed TOF of 11.8 h$^{-1}$ and 14% conversion of 4-methylstyrene with the formation of a mixture of methyl 2-phenylproprionate and methyl 3-phenylproprionate with selectivity of 60% and 40% respectively. The alkoxycarbonylation products were then isolated by separating the catalyst by filtration and removing the solvents and remaining styrene by distillation.

EXAMPLE 13

Alkoxycarbonylation of Styrene

A 50 ml stirred autoclave was charged with the following reactants

Styrene: 14.4 mmol

SAP Catalyst A: 150 mg

Water content of the catalyst=40% (made by controlled addition of water to the catalyst)

Methanol: 1 ml

Cyclohexane: 22 ml

The contents of the autoclave were flushed with nitrogen and then many times with carbon monoxide. Thereafter, the contents were heated to 75° C. After the temperature is attained, the autoclave was pressurized to 500 psig with carbonmonoxide, stirring started. For preparation of final methyl phenyl propionate product, the pressure in the autoclave was maintained constant and the progress of the reaction was monitored by observing the pressure drop and by liquid sampling. The reaction was continued for 12 hours. The reactor was then cooled and the liquid phase analysed by gas chromatography. The GC analysis showed TOF of 3.53 h$^{-1}$ and 4.5% conversion of styrene with the formation of a mixture of methyl 2-phenylproprionate and methyl 3-phenylproprionate with selectivity of 51.6% and 48.39% respectively. The alkoxycarbonylation products were then isolated by separating the catalyst by filtration and removing the solvents and remaining styrene by distillation.

EXAMPLE 14

Alkoxycarbonylation of Styrene

A 50 ml stirred autoclave was charged with the following reactants

Styrene: 14.4 mmol

SAP Catalyst B: 150 mg

Methanol: 1 ml

Cyclohexane: 22 ml

The contents of the autoclave were flushed with nitrogen and then many times with carbon monoxide. Thereafter, the contents were heated to 75° C. After the temperature is attained, the autoclave was pressurised to 500 psig with carbonmonoxide, stirring started. For preparation of final methyl phenyl propionate product, the pressure in the autoclave was maintained constant and the progress of the reaction was monitored by observing the pressure drop and by liquid sampling. The reaction was continued for 12 hours. The reactor was then cooled and the liquid phase analysed by gas chromatography. The GC analysis showed TOF of 1.01 h$^{-1}$ and 1.22% conversion of styrene with the formation of a mixture of methyl 2-phenylproprionate and methyl 3-phenylproprionate with selectivity of 61.69% and 38.3% respectively. The alkoxycarbonylation products were then isolated by separating the catalyst by filtration and removing the solvents and remaining styrene by distillation.

EXAMPLE 15

Alkoxycarbonylation of Styrene

A 50 ml stirred autoclave was charged with the following reactants

Styrene: 14.4 mmol

SAP Catalyst A: 150 mg

TsOH: 0.10526 mmol

Methanol: 1 ml

Toluene: 22 ml

The contents of the autoclave were flushed with nitrogen and then many times with carbon monoxide. Thereafter, the contents were heated to 100° C. After the temperature is attained, the autoclave was pressurised to 500 psig with carbonmonoxide, stirring started. For preparation of final methyl phenyl propionate product, the pressure in the autoclave was maintained constant and the progress of the reaction was monitored by observing the pressure drop and by liquid sampling. The reaction was continued for 12 hours. The reactor was then cooled and the liquid phase analysed by gas chromatography. The GC analysis showed TOF of 2.6 h$^{-1}$ and 3.1% conversion of styrene with the formation of a mixture of methyl 2-phenylproprionate and methyl 3-phenylproprionate with selectivity of 48% and 52% respectively. The alkoxycarbonylation products were then isolated by separating the catalyst by filtration and removing the solvents and remaining styrene by distillation.

EXAMPLE 16

Alkoxycarbonylation of Styrene

A 50 ml stirred autoclave was charged with the following reactants

Styrene: 14.4 mmol

SAP Catalyst A: 150 mg

TsOH: 0.10526 mmol

Methanol: 1 ml

Cyclohexane: 22 ml

The contents of the autoclave were flushed with nitrogen and then many times with carbon monoxide. Thereafter, the contents were heated to 100° C. After the temperature is attained, the autoclave was pressurized to 500 psig with carbonmonoxide, stirring started. For preparation of final methyl phenyl propionate product, the pressure in the autoclave was maintained constant and the progress of the reaction was monitored by observing the pressure drop and by liquid sampling. The reaction was continued for 12 hours. The reactor was then cooled and the liquid phase analysed by gas chromatography. The GC analysis showed TOF of 3.5 h$^{-1}$ and 4.2% conversion of styrene with the formation of a mixture of 2- and 3-methylphenylpropionates with selectivity of 45% and 55% respectively. The alkoxycarbonylation products were then isolated by separating the catalyst by filtration and removing the solvents and remaining styrene by distillation.

Advantages of the Invention

1. Employment of supported aqueous phase palladium complexes for alkoxycarbonylation of olefins for the first time
2. Provides good yields and selectivity to carboxylic acid esters
3. Provides simple and efficient catalyst separation and recycle

We claim:

1. A process for the preparation of a carboxylic acid ester of the general formula II,

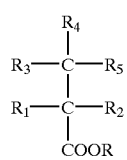

Formula II wherein R is alkyl or aryl, $R_1$ is aryl, substituted aryl, naphthyl or substituted naphthyl or alkyl, $R_2$, $R_3$, $R_4$ and $R_5$ are independently hydrogen or alkyl, said process comprising reacting an olefin of the general formula I

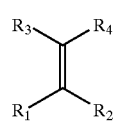

Formula I wherein, $R_1$ is aryl, substituted aryl, naphthyl or substituted naphthyl or alkyl, $R_2$, $R_3$, and $R_4$ are independently hydrogen or alkyl, in the presence of an alcohol and an organic solvent and a supported aqueous phase palladium complex catalyst, in presence or absence of a protonic acid and an alkali metal halide, under carbon monoxide atmosphere, at a temperature ranging between 30 to 130° C., for a period ranging between 1–72 hours, at pressures ranging between 50 to 1500 psig, cooling the reaction mixture to ambient temperature, depressurising the reactor, flushing the reaction vessel with inert gas, separating the catalyst by filtration and removing the solvent and isolating the compound of formula II.

2. A process as claimed in claim 1 wherein the catalyst used comprises a water-soluble palladium complex with or without free sufonated phosphine ligand.

3. A process as claimed in claim 2 wherein the water soluble palladium complex used are selected from the group consisting of any of Pd(II) and Pd(0) compounds of the type Pd$^{II}$(OAc)$_2$P$_2$, Pd$^{II}$P$_2$Cl$_2$, Pd$^{II}$P$_3$Cl]$^+$Cl$^-$, Pd$^0$P$_2$, Pd$^0$P$_3$ and mixtures thereof; wherein P is a sulfonated phosphine ligand; or a complex of the general formula III

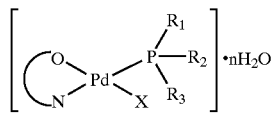

Formula III wherein $R_1$, $R_2$ and $R_3$ are substituents on the phosphine ligand and selected from the group consisting of alkyl, aryl, arylalkyl, cycloaliphatic, at least one of which carries a sulfonic acid, and salts thereof, X is aryl or alkyl sulfonato or aryl or alkyl carboxylate or formato or halides such as Cl$^-$, Br$^-$, I$^-$,

is an anionic chelating ligand containing a N donor and O$^-$ group.

4. A process as claimed in claim 3 wherein said anionic chelating ligand is selected from the group consisting of 8-hydroxyquinoline, 2-hydroxypyridine, (2-hydroxyethyl)pyridine, pyridil-2-, pyrezyl-2, piperidyl-2-, piperzyl-2-, quinolyl-2-, isoquinolyl-1- and isoquinolyl-2-carboxylates, particularly pyridyl-2-carboxylate, piperidyl-2-carboxylate and 8-hydroxyquinoline.

5. A process as claimed in claim 3 wherein the support used for the preparation of the supported aqueous phase palladium complex catalyst is selected from porous or non-porous silica.

6. A process as claimed in claim 3 wherein the sulfonated phosphorous ligand used for the preparation of the supported aqueous phase catalyst comprises a sulfonated mono phosphine.

7. A process as claimed in claim 6 wherein the sulfonated mono phosphine is selected from the group consisting of tris(sodium 3-sulfonatophenyl)phosphine (TPPTS), phenylbis(sodium-3-sulfonatophenyl)phosphine (TPPDS), diphenyl (sodium-3-sulfonatophenyl)phosphine (TPPMS), methylbis(3-sulfonatophenyl)phosphine, cyclohexylbis (sodium-3-sulfonatophenyl)phosphine, isopropyl bis (sodium-3-sulfonatophenyl)phosphine, dimethyl(sodium-3-sulfonatophenyl)phosphine and dicyclohexyl (3-sulfonatophenyl)phosphine.

8. A process as claimed in claim 6 wherein the amount sulfonated phosphine ligand used per gram mole of palladium for the preparation of the supported aqueous phase palladium catalyst is 1–20 moles.

9. A process as claimed in claim 8 wherein the amount sulfonated phosphine ligand used per gram mole of palladium for the preparation of the supported aqueous phase palladium catalyst is 2–6 moles.

10. A process as claimed in claim 1 wherein the protonic acid used for the alkoxycarbonylation reaction is selected from hydro halic acids or a protonic acids.

11. A process as claimed in claim 10 wherein the hydrohalic acid is selected from the group consisting of hydrochloric acid, hydrobromic acid and hydro iodic acid.

12. A process as claimed in claim 10 wherein the protonic acid is selected from the group consisting of para toluene sulphonic acid, methane sulphonic acid, triflouromethane sulphonic acid, formic acid, oxalic acid, acetic acid and trifluoro acetic acid.

13. A process as claimed in claim 1 wherein the halide source used for the alkoxycarbonylation reaction a halide salt or a hydrohalic acid.

14. A process as claimed in claim 13 wherein the halide salt is selected from the group consisting of lithium chloride, sodium chloride, potassium chloride, lithium iodide, lithium bromide, sodium bromide, sodium iodide, potassium bromide, potassium iodide, tetrabutylammonium chloride, tetrabutylammonium bromide and tetrabutylammonium iodide.

15. A process as claimed in claim 13 wherein the hydrohalic acid is selected from the group consisting of hydrochloric acid, hydrobromic acid and hydroiodic acid.

16. A process as claimed in claim 1 wherein the alcohol used for the alkoxycarbonylation reaction is selected from the group consisting of methanol, ethanol, n-or iso propanol, n-, iso- or tert-butanol, higher alcohols and phenols.

17. A process as claimed in claim 1 wherein the organic solvent for the alkoxycarbonylation reaction is selected from the group consisting of cyclohexane, benzene, toluene, xylenes, petroleum ether, hexane, heptane and decane.

18. A process as claimed in claim 1 wherein the concentration of catalyst is one mole of catalyst for every 50 to 50000 moles of substrate.

19. A process as claimed in claim 18 wherein the concentration of the catalyst is 1 mole of catalyst for every 100 to 10000 moles of substrate.

20. A process as claimed in claim 19 wherein the concentration of the catalyst is one mole of catalyst for every 150 to 5000 moles of substrate.

21. A process as claimed in claim 1 wherein the amount of halide source if used per gram mole of catalyst is in the range of 1 to 50 moles.

22. A process as claimed in claim 21 wherein the amount of halide source if used is 5 to 10 moles.

23. A process as claimed in claim 1 wherein amount of acid source if used per gram mole of catalyst is in the range of 1 to 50 moles.

24. A process as claimed in claim 23 wherein the amount of acid source if used per gram mole of catalyst is 5 to 10 moles.

25. A process as claimed in claim 1 wherein the reaction is carried out in a stirred reactor with the catalyst used with a suitable solvent in the presence of carbon monoxide.

* * * * *

UNITED STATES PATENT AND TRADEMARK OFFICE
CERTIFICATE OF CORRECTION

PATENT NO. : 6,479,693 B2
DATED : November 12, 2002
INVENTOR(S) : Jayasree Seayad et al.

It is certified that error appears in the above-identified patent and that said Letters Patent is hereby corrected as shown below:

<u>Title page, Item [54] and Column 1, line 2,</u>
After "ACID" insert -- ESTER --.

Signed and Sealed this

Twenty-fifth Day of March, 2003

JAMES E. ROGAN
*Director of the United States Patent and Trademark Office*